United States Patent [19]

Waters et al.

[11] Patent Number: 5,177,269

[45] Date of Patent: Jan. 5, 1993

[54] REMOVAL OF GUAIACOL FROM CRESYLIC ACID FEEDSTREAMS BY HEATING WITH A STRONG ACID

[75] Inventors: John A. Waters, Houston; James A. Brient, Missouri City, both of Tex.

[73] Assignee: Merichem Company, Houston, Tex.

[21] Appl. No.: 900,858

[22] Filed: Jun. 18, 1992

[51] Int. Cl.⁵ .................... C07C 37/70; C07C 37/74
[52] U.S. Cl. ................................. 568/761; 568/749; 568/750; 568/753
[58] Field of Search .............. 568/579, 749, 750, 753, 568/761

[56] References Cited

U.S. PATENT DOCUMENTS

| 2,697,732 | 12/1954 | Mavity | 260/613 |
| 2,807,654 | 9/1957 | Grimmett et al. | 568/749 |
| 4,420,642 | 12/1983 | Filipasic et al. | 568/753 |
| 4,447,657 | 5/1984 | Firth et al. | 568/783 |
| 4,473,713 | 9/1984 | Ratton | 368/424 |

FOREIGN PATENT DOCUMENTS 0151442 10/1981 Fed. Rep. of Germany ...... 568/749

OTHER PUBLICATIONS

J. Lawson and M. Klein, "Influence of Water on Guaiacol Pyrolysis", Ind Eng. Chem. Fundam. 1985, 24:203-208.

R. Ceylan and J. Bredenberg, "Hydrogenolysis and Hydrocracking of the Carbon-Oxygen Bond. 2. Thermal Cleavage of the Carbon-Oxygen Bond in Guaiacol", Fuel, 1982, 61:377.

A. Vuori and J. Bredenberg, "Hydrogenolysis and Hydrocracking of the Carbon-Oxygen Bond. 4. Thermal and Catalytic Hydrogenolysis of 4-Propylguaiacol", Holzforschung. 1984, 38:133-140.

Primary Examiner—Werren B. Lone
Attorney, Agent, or Firm—John R. Kirk, Jr.; Mark A. Oathout; Gordon T. Arnold

[57] ABSTRACT

A process is described for the removal of guaiacol from naturally occurring cresylic acid feed by heating the feed with a strong acid, particularly hydrochloric acid or sulfuric acid, to produce a purified cresylic acid product essentially free of guaiacol and other methoxy aromatic compounds without significant loss of cresylic acid product.

13 Claims, No Drawings

REMOVAL OF GUAIACOL FROM CRESYLIC ACID FEEDSTREAMS BY HEATING WITH A STRONG ACID

FIELD OF THE INVENTION

This invention relates to a process for removing alkoxyaromatic impurities, particularly guaiacol, from naturally occurring cresylic acid feeds by heating with a strong acid, particularly hydrochloric acid or sulfuric acid.

BACKGROUND OF THE INVENTION

Cresylic acid is an important commercial product widely used in the manufacture of chemical, agrichemical, pharmaceutical, and industrial intermediate products. Unfortunately, very few cresylic acid members are commercially synthesized. For example, the lowest molecular weight member of the cresylic acid family, phenol, is produced synthetically in very large quantities. Similarly, the methylphenols (known as cresols) are also produced synthetically, but in much smaller quantities. On the other hand, the dimethylphenols (known as xylenols) and other alkylated phenols are not commercially synthesized to any appreciable extent with the exception of 2, 6-xylenol. As such, the majority of cresylic acid isomers used in industry today are recovered from natural sources, such as partially refined petroleum and coal via coking, gasification, and liquefaction.

The cresylic acid recovered from these sources, however, is heavily contaminated with aromatic organic compounds including hydrocarbons containing heteroatoms such as nitrogen, sulfur, and oxygen. These impurities must be removed in order to make marketable products. Methoxy-substituted phenols, such as guaiacol and methyl guaiacol, comprise a particularly troublesome group of contaminants. Since guaiacol, an orthomethoxy phenol, boils near the boiling points of meta-cresol and para-cresol, and methyl guaiacol, a methoxy cresol, boils in the range of xylenols, they cannot be separated from the cresylic acid fractions by conventional distillation. The presence of such methoxyaromatic impurities significantly reduces the commercial value of cresylic acid as a raw material for high quality plastics and resins. To be useful, the various isomers of cresylic acid must be separated from these impurities and often from each other, and therein lies the problem because, heretofore, there has been no simple process for physically or chemically separating guaiacols from cresylic acid. In the past, the guaiacol was destroyed in the presence of the cresylic acid but with a considerable decrease in cresylic acid yield. Moreover, such destruction had been accomplished only with much difficulty and with the resultant loss of cresylic acid yield to byproducts, most of them unwanted heavies and coke.

Considerable academic research has been reported relating to removal of methoxy compounds and to the demethylation of phenols. This work is reported in articles, such as J. Lawson and M. Klein, "Influence of Water on Guaiacol Pyrolysis," *Ind. Eng. Chem. Fundam.*, 24:203, 1985; R. Ceylan and J. Bredenberg, "Hydrogenolysis and Hydrocracking of the Carbon-Oxygen Bond.2. Thermal Cleavage of the Carbon-Oxygen Bond in Guaiacol," *Fuel*, 61:377, 1982; and A. Vuori and J. Bredenberg, "Hydrogenolysis and Hydrocracking of the Carbon-Oxygen Bond. 4. Thermal and Catalytic Hydrogenolysis of 4Propylguaiacol," *Holzforschung*, 38:133, 1984. Likewise, a dealkylation process involving the reaction of acetic acid in the presence of an alumina-silica catalyst in the liquid phase is described in U.S. Pat. No. 2,697,732. The rearrangement of alkyl phenyl ethers to ortho-alkyl phenols by heating at temperatures from 75° C. to 200° C. in the presence of alumina is described in U.S. Pat. No. 4,447,657. A process for the hydrolysis of alkyl-aryl ethers in the presence of a carboxylate, preferably an alkali metal carboxylate, catalyst is described in the U.S. Pat. No. 4,473,713. Notwithstanding the considerable amount of investigation of this problem of guaiacol removal, a totally satisfactory result remains to be found. It is an object of this invention to provide a process for the destruction of guaiacol in the presence of cresylic acids so they may be used for other purposes.

SUMMARY OF THE INVENTION

This invention is a process for the removal of guaiacol impurities from a naturally occurring cresylic acid feedstream, especially for a feedstream derived from lignite sources, by heating the feed in the presence of a strong acid, to produce a purified cresylic acid product essentially free of guaiacol and other methoxy aromatic compounds without significant loss of cresylic acid product or coke formation. Strong acids useful in the practice of this invention include those having a dissociation constant, K, greater than about $10^{-2}$ or, said another way, a pK of less than about 2. Some strong acids will remove the guaiacol but may add other contaminants which are undesirable, such as, for example, nitric acid. Classes of acids such as the halogen acids, organosulfonic acids and other mineral acids, i.e. sulfuric and phosphoric acid, are preferred.

The process is normally practiced at a temperature range of from about 50° C. to about 350° C. for a sufficient time period normally from about 1 hour to about 2½ hours, depending upon acid strength, ratio of acid to feed and temperature. Pressure is normally a function of the temperature of the contents of the closed reactor. Acid strength ranges from about 10% to about 50% by weight and the acid/cresylic acid ratio, from about 1:10 to about 1:30 by weight (based upon 100% acid), in the reaction to improve guaiacol reduction, while preventing unwanted by-product formation, and coke and gas formation. Variations in the cresylic acid feed matrix, depending upon the source and guaiacol levels in the feed, are also considered in determining the reaction conditions to select.

DETAILED DESCRIPTION OF THE INVENTION

This invention is a process for the purification of naturally occurring cresylic acid mixtures recovered from the pitch residue in the removal of liquids from coal, coal tars, lignite, or natural gas condensates. These naturally occurring cresylic acid-containing mixtures include several species of methoxyaromatic impurities, particularly guaiacol, which is often present in amounts up to about 4% and sometimes about 6% by weight in feed material which comes from a lignite source and about 2% where the feed material for the practice of this invention is recovered from coal or coal tar. The process of this invention would successfully operate to eliminate even greater amounts of guaiacols in naturally occurring feeds and should not be considered limited to one containing 4% by weight.

To begin, the crude feed is usually treated to remove residual pitch and distilled to remove phenols and low-boiling hydrocarbons, i.e., those materials which have boiling points below or near that of the phenol being removed. The feed is then heated in a closed vessel in the presence of a strong aqueous acid, preferably hydrochloric acid or sulfuric acid, usually with agitation, as more particularly described below. The guaiacol feed has been found to normally contain aromatic nitriles and other nitrogen-containing aromatics which are damaging to the final commerical interests of the cresylic acid materials contained in the feed.

While hydrochloric and sulfuric acid are especially preferred in the practice of this invention, it should be understood that strong acids useful in the practice of this invention includes those having a dissociation constant, K, greater than about $10^{-2}$. Classes of such acids include the halogen acids, organosulfonic acids and other mineral acids, particularly sulfuric and phosphoric acid. Those skilled in the art desiring to produce cresylic acid mixtures readily useful in other processes would, of course, know to avoid certain strong acids even though they fit within the criteria set forth above if side reactions or byproduct creation results in a product which is not satisfactory. For example, even though nitric acid has a dissociation constant within the range which would cause the removal of the guaiacol from the system, the residual presence of nitrates would cause it to be unacceptable. Those skilled in the art would recognize this and reject certain acids, even though operable to cause guaiacol removal. For those desiring to remove only the guaiacol without particular criteria concerning the presence of other, normally undesirable, constituents the invention described herein may be practiced utilizing such other acids. As will be seen hereinafter, it is the degree of dissociation of the acid and not the concentration of the acid which is important in connection with the practice of this invention. Using the disclosure which follows and the specific examples in connection with the degree of dilution of sulfuric acid and hydrochloric acid, knowing the strengths of such acid which are commercially available, one of ordinary skill in the art can readily determine the concentrations of the above-identified strong acids useful in the practice of this invention.

In the reaction of this process itself, the presence of water or the presence of certain acids may result in side reactions which may produce unwanted results. For example, the presence of water when sulfuric acid is used suppresses the sulfonation and oxidation reaction which destroys the guaiacol while, in the use of hydrochloric acid and phosphoric acid, the water reduces reaction of the methyl and ethyl groups split from the alkoxy aromatic impurity which results in the tar formation. In practicing the invention a balance may be determined from converting the alkoxy groups in the guaiacol and the unwanted formation of tars which polymerize from the ions created in the reaction.

In its broad context, the practice of this invention would occur in a batch reactor, preferably one impervious to attack by dilute aqueous solutions of strong acids. A polytetrafluoroethylene-coated reactor would be a likely candidate for use in the practice of this invention since the strong acids used, normally hydrochloric or sulfuric acids are used in a more or less dilute form and are therefore highly corrosive to almost all common metals used in construction. Of course, a glass-lined reactor could be used but it is a fragile piece of equipment. The strong acid is used in an aqueous form, normally from about 10% to about 40% by weight, preferably from about 25% to about 35% by weight, particularly when the strong acid is sulfuric acid. The preferred strength of the hydrochloric acid would preferably range from about 20% to about 38% by weight. The aqueous acid, in the strength as described above, is added to the reactor containing the feed stream in an amount such that the aqueous acid is present in the mixture in an amount of from about 1:10 to about 1:30 parts acid by weight (based upon 100% acid) to the parts cresylic acid feed by weight. Preferably, the ratio is from about 1:15 to about 1:25 (100% basis). Of course, the more acid per weight of feed present, the faster the reaction would occur, and therefore the lower the temperature. It has been found, however, that when sulfuric acid is used as the strong aqueous acid, with insufficient water present, sulfonation of the aromatic molecule occurs and thus, even though there is substantially 100% conversion of the guaiacol present in the mix, the sulfonated aromatics diminish the yield of the cresylic acid. Surprisingly, the demethylation of the guaiacols with sulfuric acid has also been found to remove nitriles present in the crude feed stream.

Once the reactants are present together, the reaction vessel would be closed and rendered pressure-tight and brought to a temperature of from about 50° C. to about 350° C., preferably from about 150° C. to about 225° C. and, preferably with stirring, allowed to react for an effective period of time, preferably from about 1 to about 2½ hours, more preferably from about 1½ to about 2 hours. Of course, the time and temperature, as well as the strength of the aqueous solution of the strong acid used, determine the results of the guaiacol removal and the amount of byproducts or tars formed. It has been discovered that the higher concentration of the strong acid results in loss of yield whereas lower concentrations of the strong acid result in incomplete conversion of the guaiacol. Substantially complete conversion of the guaiacol occurs at acid strengths greater than 25% $H_2SO_4$ by weight. The pressure in the reaction vessel would normally be autogenous pressure for the temperature and reaction conditions run but would be found to vary from about 100 psig to about 300 psig. The cresylic acid feeds will react differently under the process of this invention. The optimum conditions for the elimination of guaiacol within the foregoing parameters can readily be determined by routine experimentation, given the description of this invention.

Once the reaction is complete or the selected amount of time had passed, the reactor and its content are cooled. This cooling could be accomplished in any number of ways well known to those of ordinary skill in the art either by internal coils or flashing the reaction mixture into another vessel, or the like. Should the temperature not be reduced fairly rapidly, the presence of the strong acid, particularly sulfuric acid, results in further reaction to form unwanted by-products and loss in yield of the cresylic acid product.

It is preferred that the cresylic acid, now substantially free of guaiacol, be separated from the acid by solvent extraction of the organic product from the aqueous phase containing the acid. Virtually any of the well known water-immiscible solvents for such cresylic acid-containing materials could be used but it is preferred that diisopropyl ether be used to separate the organic layer from the aqueous layer present in the reaction mixture. The diisopropyl ether, or organic phase, is separated from the aqueous phase and flashed or distilled in another appropriate manner to remove the solvent diisopropyl ether from the cresylic acid product being substantially free of not only guaiacols but of nitrogen-containing aromatic compounds previously present in the reaction mixture. The guaiacol was shown to be hydrolyzed to phenol and catechol and byproducts included xylenols and methyl anisoles, as well as high molecular weight coupled cresols. Impurity formation appeared to be a function of guaiacol conversion, both in amount and type of impurity produced.

After the optimum set of reaction conditions had been determined from the synthetic mixture of meta-, para-cresol containing guaiacol, hydrolysis of guaiacol in naturally occurring depitched cresylic acid was performed. Removal of guaiacol from this source by heating with sulfuric acid was not quite as effective as from synthesized mixture of meta-, para-cresol and guaiacol, but nitrogen compounds were reduced by 98%. In a further embodiment, a nitrile (o-tolunitrile) also added to the mixture was completely hydrolyzed under the conditions used in order to demonstrate the effectiveness of the process to also remove nitrogen-containing materials. o-Tolunitrile has been found to be the nitrile least susceptible to acidic hydrolysis.

The following examples are introduced to further illustrate the present invention but not with the intention of unduly limiting the same. The reactions were run in a closed, polytetrafluorethylene-lined autoclave to minimize corrosion problems.

EXAMPLES

I. Hydrochloric Acid

To demonstrate one preferred embodiment of this invention, 25 g of concentrated (38% by weight) hydrochloric acid was added to a 111 g sample prepared from a naturally occurring cresylic acid stream recovered from lignite containing 4.37% guaiacol (weight ratio of feed to acid (100% acid basis)=14.8/1). The mixture was placed in the autoclave which was closed and heated, with stirring, at a temperature of about 150° C. for two hours. The pressure was measured to be about 100 psig. After the mixture was allowed to cool, 200 ml of water and 300 ml toluene were added to obtain good phase separation. The reaction product was purple—a sign that catechol had been liberated. The toluene layer was then neutralized with about 5 g of sodium carbonate ($Na_2CO_3$) and filtered. The toluene was removed by a rotary evaporator and the cresylic acid distilled at a temperature of 110° C. and a pressure of 1 mm Hg. The recovered cresylic acid product weighed 94 g (a yield of 87% in terms of cresylic acid in the feed). The guaiacol concentration in this product, however, amounted to only 0.031% or 310 parts per million, a 99.3% reduction. Moreover, little or no tars were formed.

II. Sulfuric Acid

A series of eleven sulfuric acid hydrolyses of guaiacol were run in a 750 ml Berghof lined closed autoclave. The reaction temperature ranged from about 150° C. to 200° C. for the various runs. Reactor pressure was maintained at about 150±20 psig. A standard synthetic feed mixture of 100 g meta-, para-cresol containing 4% guaiacol was used in most of the runs. Two runs used a depitched naturally occurring cresylic acid mixture containing about 1.3% guaiacol. Also added to several of the synthetic feed mixture was 1% o-tolunitrile. The aqueous sulfuric acid used varied from 10% to 35% by weight $H_2SO_4$, at a cresylic acid/mineral acid (wt:wt) ratio of 10/1 or 20/1. The autoclave set point was 180° C., but reactor pressure was monitored to maintain about 150° to 200° C. In two runs, a leaking seal in the autoclave caused a significant loss of water during the run, with the resulting concentrated sulfuric acid causing greater byproduct formation. Following such reaction, the products were cooled by applying external cooling to the autoclave.

Acid strength, mineral acid/cresylic acid ratio, and reaction temperatures were varied to determine optimum reaction conditions for a batch process. Temperatures were calculated from pressure readings and vapor pressure data. Early runs were controlled by maintaining about 150 psig; later runs were maintained at 180° C. or 200 psig. The results and run conditions of the experiment are reported in Table I.

TABLE I

Sulfuric Acid Hydrolysis of Guaiacol

| Run | $H_2SO_4$, % | Pressure Range, psig | Conversion, % | Guaiacol, Area % Feed | Guaiacol, Area % Product | By-products[3] |
|---|---|---|---|---|---|---|
| A. Hydrolysis of 4 wt % Guaiacol in meta-, para-Cresol | | | | | | |
| 1 | 10[1] | 160-295 | 30.9 | 3.25 | 2.25 | 0.3 |
| 2 | 25 | 140-170 | 41.9 | 3.26 | 1.89 | 0.9 |
| 3 | 25[1] | 130-160 | 75.5 | 3.22 | 0.79 | 1.5 |
| 4 | 25[2] | 120-150 | 98.6 | 3.21 | 0.05 | 2.0 |
| 5 | 30 | 150-170 | 85.3 | 3.20 | 0.47 | 2.7 |
| 6 | 30 | 190-240 | 99.1 | 3.30 | 0.03 | 7.6 |
| 7 | 35 | 120-150 | 90.3 | 3.00 | 0.29 | 3.5 |
| 8 | 35 | 140-170 | 97.7 | 3.25 | 0.07 | 5.1 |
| 9 | 35[2] | 140-160 | 98.9 | 3.02 | 0.03 | 8.5 |
| B. Hydrolysis of Guaiacol in depitched Cresylic Acid | | | | | | |
| 10 | 35 | 110-130 | 60.0 | 1.33 | 0.53 | |
| 11 | 35 | 180-220 | 89.3 | 1.38 | 0.15 | |

[1] 20:1 cresylic acid:conc. $H_2SO_4$ (w:w) for one hour; all other runs used 10:1 cresylic acid:conc. $H_2SO_4$ (w:w) for two hours reaction time
[2] A leaking o-ring seal caused a substantial loss of water. Actual acid concentration was higher than intended.
[3] Byproducts total includes phenol, xylenols, anisoles, and coupled cresols but does not include catechol, which was not detected by the analytical method The crude products were extracted with 300 g diisopropyl ether (DIPE) to aid phase separation, and then washed twice with 50 g deionized water. An insoluble oil and rag layer were observed in reactions with high guaiacol conversion, and these unknowns (probably high molecular weight compounds) were retained with the organics during phase separation. Samples obtained during the reactions were likewise extracted with DIPE and water washed prior to analysis. The crude product from the runs using depitched cresylic acid crude mixture as a feed was continuously vacuum flashed at 100 mm Hg after decanting the aqueous acid layer. No extraction or neutralization of the organics was done before the distillation.

Samples were analyzed by gas chromatography on a 30 meter fused silica SP-1000 column at 160° C. isothermal. This column did not separate phenol+ortho-cresol or 2,4 xylenol+para-cresol, and catechol was not detected by this method. Analyses for catechol were made on a 30 meter Durabond-5 column at 60° C. after derivatizing the sample with N,N-bis (trimethylsilyl) acetamide. Confirmatory GC/MS analyses were performed using a 30 meter SP-1000 column at 140° C. programmed to 210° C. at 6°/minute.

Guaiacol removal from cresylic acid increased linearly with increasing acid strength when reaction time and temperature were held constant. Where 30% to 35% $H_2SO_4$ was used, a 10:1 (wt:wt) ratio of cresylic acid to sulfuric acid mixture was in the autoclave for 2 hours. The data showed that a 1 to 2 hour reaction time at from 180° to 200° C. and 150 to 200 psig using at least 35% sulfuric acid was required to remove more than 98% of the guaiacol from a synthetic guaiacol/meta-, para-cresol feed mixture. Higher conversion of guaiacol using more dilute acid could be obtained if the reaction temperature and pressure were raised. The reactions were monitored by reactor pressure since accurate temperature readings were not possible in most cases. In runs using 30% to 35% sulfuric acid where accurate temperatures were obtained, about 170° C. produced about 170 psig reactor pressure, about 200° C. produced about 200 psig, and about 215° C. gave about 220 psig. In all cases, o-tolunitrile was reduced to trace or non-detectable levels by the aqueous sulfuric acid hydrolysis.

Hydrolysis of guaiacol in depitched cresylic acid was run as described above after reaction conditions had been determined using synthetic mixtures of guaiacol in meta-, para-cresol. The naturally occurring cresylic acid sample was analyzed to contain about 60% phenol, about 26% meta-, para-cresol, about 1.3% guaiacol, and about 1.7% nitrogen compounds. The reaction, which was run as before using 35% sulfuric acid at about 200° C. to 210° C., removed only 89% of the guaiacol during the two hour run, as opposed to 90% to 98% removal from the synthetic feed mixture at those conditions.

Nitrogen compounds were reduced to about 400 ppm or about 40 ppm, depending on the sample work-up method used. Distilling sulfuric acid-treated cresylic acids without removing the residual acid resulted in extensive tar formation. The aqueous acid phase recovered after the reaction was only 50% to 75% of the weight of acid charged, indicating a large amount was soluble in the organics. The reaction products from the guaiacol/meta-, para-cresol feed were extracted with diisopropyl ether as described above and washed with water prior to distillation. Nitrogen compounds in the solvent-extracted product totalled about 1000 ppm. Acid-treated cresylic acid containing residual sulfuric acid was flashed (at 100 mm Hg) in a continuous distillation to give a product containing only 55 ppm nitrogen compounds. Greater than 85% of the distillation charge was recovered overhead leaving nitrogen-bases, sulfuric acid, and heavy byproducts in the bottoms. The overall net yield of cresylic acid from the combination of the hydrolysis and vacuum flash was estimated to be 87%.

Extensive amounts of byproducts were formed during acid hydrolysis of guaiacol. The data in Table I indicate the dramatic increase in impurity levels as the conversion of guaiacol increased (runs 6, 8 and 9). The total impurity level (exclusive of catechol, which could not be detected by the analytical method used) was less than 1% at low guaiacol conversion, but increased to near 8% of the crude product at near complete conversion. Non-cresylic acid by-products identified in the GC/MS analysis of the product were primarily methyl anisoles and several high molecular weight cresol derivatives, including ditolyl ethers (MW=198) and unknown compounds (MW=210 and 224).

The above description of embodiments and examples of this invention are given by way of example and instruction and are not intended as limitations to the claims which follow since further embodiments and changes will occur to those of skill in the art after reading the above description of the present invention.

What is claimed is:

1. A process for removing guaiacol impurities from a naturally occurring cresylic acid mixture which comprises the steps of:
   heating the cresylic acid mixture for a sufficient period of time in the presence of an aqueous solution of a strong acid at a temperature of from about 50° C. to about 350° C. at autogenous pressure;
   cooling the mixture; and
   recovering the cresylic acid product from the mixture.

2. The process of claim 1 wherein the strong acid is hydrochloric acid.

3. The process of claim 1 wherein the strong acid is sulfuric acid.

4. The process of claim 3 wherein the sulfuric acid is in the form of an aqueous solution containing from about 10% to about 40% by weight $H_2SO_4$.

5. The process of claim 1 wherein the cresylic acid product is recovered from the reaction mixture by solvent extraction.

6. The process of claim 5 wherein the solvent is diisopropyl ether.

7. A process for removing guaiacol impurities from a naturally occurring cresylic acid mixture which comprises the steps of:
   heating the cresylic acid mixture in the presence of an aqueous solution of a strong acid selected from the group consisting of hydrochloric acid and sulfuric acid at a temperature of from about 50° C. to about 350° C. at autogenous pressure;
   cooling the mixture; and
   recovering the cresylic acid product from the mixture by solvent extraction wherein the solvent is diisopropyl ether.

8. The process of claim 7 wherein the strong acid is from about 20% to about 38% by weight hydrochloric acid at a temperature from about 125° C. to about 225° C. at autogenous pressure for a time of from about 1½ hours to 2½ hours.

9. The process of claim 7 wherein the strong acid is from about 30% to about 35% by weight aqueous sulfuric acid at a temperature from about 150° C. to about 250° C. at autogenous pressure for a period from about 1½ hours to 2½ hours.

10. A process for removing guaiacol impurities from a cresylic acid feed obtained from a lignite source which comprises the steps of:
    heating the feed in the presence of from about 25% to about 35% concentration by weight sulfuric acid or from about 20% to about 38% concentration by weight hydrochloric acid, present at a weight acid:weight feed ratio of from 1:10 to about 1:30, basis 100% acid, for a period of from 1½ hours to about 2 hours at a temperature of from 150° C. to about 225° C. and autogenous pressure to form a reaction mixture;
    cooling the reaction mixture;
    adding to the cooled reaction mixture a sufficient quantity of a water immiscible solvent selective for the feed in the reaction mixture allowing a phase separation to occur between the solvent containing the cresylic acid and aqueous components;
    separating the contents of the phases, recovering the solvent from the separated mixture; and distilling the solvent from the cresylic acid product being substantially free of guaiacol.

11. The process of claim 10 wherein the solvent is diisopropylether.

12. The process of claim 11 wherein the acid is sulfuric acid.

13. The process of claim 11 wherein the acid is hydrochloric acid.

* * * * *